United States Patent

Dodd et al.

(10) Patent No.: US 6,472,530 B1
(45) Date of Patent: Oct. 29, 2002

(54) BENZO-FUSED DITHIEPINO[6,5-B] PYRIDINES, AND RELATED COMPOSITIONS AND METHODS

(75) Inventors: John H. Dodd, Pittstown, NJ (US); Kenneth C. Rupert, South Orange, NJ (US); James L. Bullington, Hamilton Square, NJ (US); Daniel A. Hall, Somereset, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 64 days.

(21) Appl. No.: 09/653,024

(22) Filed: Sep. 1, 2000

Related U.S. Application Data

(60) Provisional application No. 60/155,343, filed on Sep. 22, 1999.

(51) Int. Cl.[7] .................. C07D 221/16; C07D 337/08
(52) U.S. Cl. ........................................ 546/93; 544/126
(58) Field of Search ................ 546/93; 544/106, 544/111–126

(56) References Cited

U.S. PATENT DOCUMENTS

| | | | |
|---|---|---|---|
| 4,285,955 A | 8/1981 | Wehinger et al. | |
| 4,483,985 A | 11/1984 | Wehinger et al. | |
| 4,532,248 A | 7/1985 | Franckowiak et al. | |
| 4,845,225 A | 7/1989 | Schwender et al. | |
| 4,879,384 A | 11/1989 | Schwender et al. | |
| 5,075,440 A | 12/1991 | Wustrow et al. | |
| 5,708,177 A | 1/1998 | Staub | |
| 6,291,454 B1 | 9/2001 | Bullington et al. | |

FOREIGN PATENT DOCUMENTS

| | | |
|---|---|---|
| JP | 58201764 | 11/1983 |

OTHER PUBLICATIONS

English Abstract WO 2001092267, DN 136:20094 Preparation of dihydropyridines . . . Dec. 6, 2001.*
Dodd et al., Drug Des. Discov. 1997 15:135–48.
Dodd et al., Drug Des. Discov. 1993, 10:65–75.
Pagani, G.P.A., J. Chem. Soc. Perkin Trans. 2, 1392 (1974).
Biggadike et al., 2000, J. Med. Chem. 43:19–21.
Lee et al., 1998, Curr. Opin. Drug Disc. Dev. 1: 235–44.
Edema et al. J. Org. Chem. 58: 5624–7, 1993.
Howard et al., J. Amer. Chem. Soc. 82:158–64, 1960).
Eistert et al. (Chem. Ber. 110, 1069–1085, 1977).
Mason et al. (J. Chem. Soc. (C) 2171–76, 1967).
E. A. Fehnel (J. Amer. Chem. Soc. 74, 1569–74, 1952).

* cited by examiner

*Primary Examiner*—Alan L. Rotman
*Assistant Examiner*—Rita Desai

(57) ABSTRACT

This invention provides novel dithiepino[6,5-b]pyridines of the following formulae:

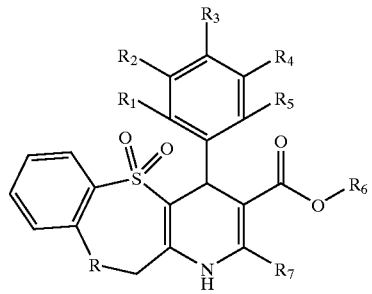

I

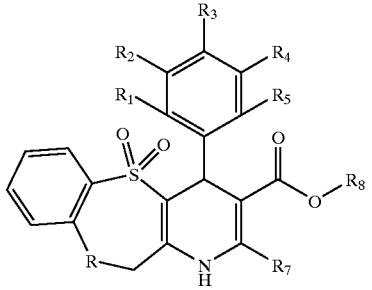

II

These compounds are useful as calcium channel antagonists with cardiovascular, antiasthmatic and antibronchoconstriction activity. Thus, this invention also provides pharmaceutical compositions, as well as methods, for preventing and treating disorders such as hypersensitivity, allergy, asthma, bronchospasm, dysmenorrhea, esophageal spasm, glaucoma, premature labor, urinary tract disorders, gastrointestinal motility disorders and cardiovascular disorders.

42 Claims, No Drawings

BENZO-FUSED DITHIEPINO[6,5-B] PYRIDINES, AND RELATED COMPOSITIONS AND METHODS

CROSS-REFERENCE TO RELATED APPLICATIONS

This application claims the benefit under 35 U.S.C. § 119(e) of provisional application Serial No. 60/155,343, filed Sep. 22, 1999 which is incorporated herein by reference.

FIELD OF THE INVENTION

This invention relates to novel benzo-fused dithiepino[6,5-b]pyridines useful as calcium channel blockers. These compounds, and related pharmaceutical compositions, are useful for treating and preventing a number of disorders such as hypersensitivity, allergy, asthma, bronchospasm, dysmenorrhea, esophageal spasm, glaucoma, premature labor, urinary tract disorders, gastrointestinal motility disorders and cardiovascular disorders.

BACKGROUND OF THE INVENTION

Thiacycloalkeno[3,2-b]pyridines are inhibitors of calcium ion uptake into smooth muscle tissue. They act to relax or prevent contraction of the tissue mediated by calcium mechanisms (Dodd et al., Drug Des. Discov. 1997 15:135–48). These compounds are active antihypertensives and bronchodilators.

Thiacycloalkeno[3,2-b]pyridines are useful for the treatment of cardiovascular disorders, including hypertension, ischemia, angina, congestive heart failure, migraines, myocardial infarction and stroke. Such compounds are also useful for the treatment of other disorders such as hypersensitivity, allergy, asthma, dysmenorrhea, esophageal spasm, gastrointestinal motility disorders, glaucoma, premature labor and urinary tract disorders.

Dodd et al. evaluated a series of thiacycloalkeno[3,2-b] pyridines ranging in sulfone ring size from five to nine members for calcium antagonist activity. It was found that increasing the sulfone ring size from 5 to 8 members results in an in vitro potency increase of two orders of magnitude. Aromatic substitution patterns which favor tracheal effects over aortic effects were found to be 2-$NO_2$ and 2-Cl, 6-F. The ester side chain which was found to maximize in vivo activity was the N-benzyl-N-methyl aminoethyl moiety (Dodd et al., Drug Des. Discov. 1997, 15:135–48, and Drug Des. Discov. 1993, 10:65–75).

Numerous compounds related to thiacycloalkeno[3,2-b] pyridines are known, as exemplified by the following publications. U.S. Pat. No. 5,708,177 to Straub discloses a process for the preparation of optically active ortho-substituted 4-aryl- or heteroaryl-1,4-dihydropyridines by oxidation and subsequent reduction from their opposite enantiomers. U.S. Pat. No. 5,075,440 to Wustrow et al. discloses pyrido[2,3-f] [1,4]thiazepines and pyrido[3,2-b] [1,5]benzothiazepines which are useful as calcium channel antagonists with cardiovascular, antiasthmatic and antibronchoconstriction activity. U.S. Pat. Nos. 4,879,384 and 4,845,225, both to Schwender and Dodd, disclose substituted thiacycloalkeno [3,2-b] pyridines which are also useful as calcium channel antagonists with cardiovascular, antiasthmatic and antibronchoconstrictor activity. U.S. Pat. Nos. 4,285,955 and 4,483,985 disclose acyclic sulfone substitution on simple dihydropyridines which possess calcium channel antagonist activity. U.S. Pat. No. 4,532,248 discloses a broad genus of dihydropyridines, including cyclic sulfones fused to a dihydropyridine nucleus. Cardiotonic activity is disclosed for the entire genus. However, the compounds disclosed in this patent are not taught to be calcium channel blockers. Finally, 10-Phenyl-2H-thiopyranol[3,2-b]quinolines are disclosed in Pagani, G. P. A., J. Chem. Soc. Perkin Trans. 2,1392 (1974).

"Soft drugs" (also known as "antedrugs") are biologically active drugs which are metabolically inactivated after they achieve their therapeutic role at their designed site of action. The use of soft drugs, instead of their non-inactivatable analogs, avoids unwanted side effects. Soft drugs are known generally (see, for example, Biggadike et al., 2000, J. Med. Chem. 43:19–21; Lee et al., 1998, Curr. Opin. Drug Disc. Dev. 1: 235–44). However, no dihydropyridine soft drugs are known.

SUMMARY OF THE INVENTION

This invention provides novel benzo-fused dithiepino[6,5-b]pyridines as defined hereinbelow, as well as methods for making same. This invention also provides a pharmaceutical composition comprising the instant compound and a pharmaceutically acceptable carrier.

This invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

Finally, this invention provides an apparatus for administering to a subject the instant pharmaceutical composition, comprising a container and the pharmaceutical composition therein, whereby the container has a means for delivering to the subject a therapeutic and/or prophylactic dose of the pharmaceutical composition.

DETAILED DESCRIPTION OF THE INVENTION

This invention provides a compound of Formula I,

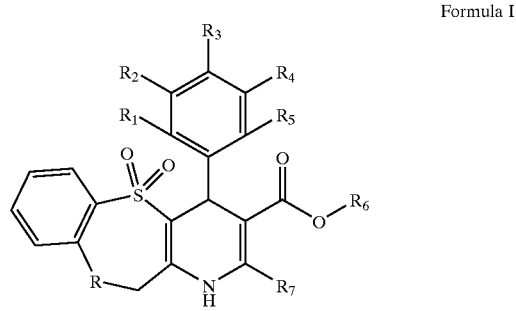

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_1$ and $R_2$);

(b) $R_6$ is selected from the group consisting of H, $C_{1-5}$ straight or branched alkyl, aryl, 3-piperidyl, N-substituted 3-piperidyl, N-substituted 2-pyrrolidinyl methylene and substituted alkyl, wherein
said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
(i) R' and R" are independently selected from the group consisting of H, $C_{1-8}$ straight or branched alkyl, $C_{3-7}$ cycloalkyl, phenyl, benzyl and phenethyl, or (ii) R' and R" together form a heterocyclic ring selected from the group consisting of piperidino, pyrrolidino, morpholino, thiomorpholino, piperazino, 2-thieno, 3-thieno and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);
(c) $R_7$ is selected from the group consisting of H, amino, alkyl, aryl, trifluoromethyl, alkoxymethyl, 2-thieno and 3-thieno; and
(d) R is SO or $SO_2$.

In one embodiment of Formula I, $R_6$ is —$(CH_2)_2N(CH_3)CH_2PH$. In another embodiment, $R_6$ is methyl. In a further embodiment $R_4$ and $R_5$ are Cl, $R_7$ is methyl, and R is SO. In yet a further embodiment, $R_5$ is Cl, $R_7$ is methyl, and R is $SO_2$.

The following compounds are preferred embodiments of the present invention:

1H-[1,5]Benzodithiepino[3,2-b]pyridine-3-carboxylic acid, 4-(2-chlorophenyl)-4,11-dihydro-2-methyl, methyl ester, 5,5,10-trioxide;
1H-[1,5]Benzodithiepino[3,2-b]pyridine-3-carboxylic acid, 4-(2,3-dichlorophenyl)-4,11-dihydro-2-methyl, 2-[methyl(phenylmethyl)amino]ethyl ester, 5,5,10,10-tetraoxide;
1H-[1,5]Benzodithiepino[3,2-b]pyridine-3-carboxylic acid, 4,11-dihydro-2-methyl-4-(2-nitrophenyl), 2-[methyl(phenylmethyl)amino]ethyl ester, 5,5,10,10-tetraoxide;
1H-[1,5]Benzodithiepino[3,2-b]pyridine-3-carboxylic acid, 4-(3-chlorophenyl)-4,11-dihydro-2-methyl, 2-[methyl(phenylmethyl)amino]ethyl ester, 5,5,10,10-tetraoxide;
1H-[1,5]Benzodithiepino[3,2-b]pyridine-3-carboxylic acid, 4-(2-chlorophenyl)-4,11-dihydro-2-methyl, methyl ester, 5,5,10,10-tetraoxide;
1H-[1,5]Benzodithiepino[3,2-b]pyridine-3-carboxylic acid, 4-(2-chlorophenyl)-4,11-dihydro-2-methyl, methyl ester, 5,5,10,10-tetraoxide;
1H-[1,5]Benzodithiepino[3,2-b]pyridine-3-carboxylic acid, 4-(3-chlorophenyl)-4,11-dihydro-2-methyl, methyl ester, 5,5,10-trioxide;
1H-[1,5]Benzodithiepino[3,2-b]pyridine-3-carboxylic acid, 4-(2,3-dichlorophenyl)-4,11-dihydro-2-methyl, methyl ester, 5,5,10-trioxide;
1H-[1,5]Benzodithiepino[3,2-b]pyridine-3-carboxylic acid, 4-(2,3-dichlorophenyl)-4,11-dihydro-2-methyl, methyl ester, 5,5,10,10-tetraoxide;
1H-[1,5]Benzodithiepino[3,2-b]pyridine-3-carboxylic acid, 4-(3-chlorophenyl)-4,11-dihydro-2-methyl, methyl ester, 5,5,10,10-tetraoxide;
1H-[1,5]Benzodithiepino[3,2-b]pyridine-3-carboxylic acid, 4,11-dihydro-2-methyl-4-(3-nitrophenyl), methyl ester, 5,5,10,10-tetraoxide;
1H-[1,5]Benzodithiepino[3,2-b]pyridine-3-carboxylic acid, 4,11-dihydro-2-methyl-4-(pentafluorophenyl), methyl ester, 5,5,10,10-tetraoxide;
1H-[1,5]Benzodithiepino[3,2-b]pyridine-3-carboxylic acid, 4,11-dihydro-2-methyl-4-(pentafluorophenyl), 2-[methyl(phenylmethyl)amino]ethyl ester, 5,5,10,10-tetraoxide;
1H-[1,5]Benzodithiepino[3,2-b]pyridine-3-carboxylic acid, 4-[2-fluoro-3-(trifluoromethyl)phenyl]-4,11-dihydro-2-methyl, methyl ester, 5,5,10,10-tetraoxide;
1H-[1,5]Benzodithiepino[3,2-b]pyridine-3-carboxylic acid, 4-[2-fluoro-3-(trifluoromethyl)phenyl]-4,11-dihydro-2-methyl, 2-[methyl(phenylmethyl)-amino]ethyl ester, 5,5,10,10-tetraoxide;
1H-[1,5]Benzodithiepino[3,2-b]pyridine-3-carboxylic acid, 4,11-dihydro-2-methyl-4-(3-nitrophenyl), methyl ester, 5,5,10,10-tetraoxide;
1H-[1,5]Benzodithiepino[3,2-b]pyridine-3-carboxylic acid, 4,11-dihydro-2-methyl-4-(3-nitrophenyl), 2-[methyl(phenylmethyl)amino]ethyl ester, 5,5,10,10-tetraoxide;
1H-[1,5]Benzodithiepino[3,2-b]pyridine-3-carboxylic acid, 4-(2-chloro-6-fluorophenyl)-4,11-dihydro-2-methyl, 2-[methyl(phenylmethyl)amino]ethyl ester, 5,5,10,10-tetraoxide;
1H-[1,5]Benzodithiepino[3,2-b]pyridine-3-carboxylic acid, 4-(2-chlorophenyl)-4,11-dihydro-2-methyl, 2-[methyl(phenylmethyl)amino]ethyl ester, 5,5,10-trioxide; and
1H-[1,5]Benzodithiepino[3,2-b]pyridine-3-carboxylic acid, 4-(2-chlorophenyl)-4,11-dihydro-2-methyl, 2-[methyl(phenylmethyl)amino]ethyl ester, 5,5,10,10-tetraoxide.

This invention also provides soft drug analogs of the compounds of Formula I. These soft drugs are characterized by a chemically labile moiety bound to the ester group in turn bound to the dihydropyridine ring structure. The soft drugs permit the instant drugs to exert their effect locally, and to subsequently be metabolized in the blood stream, thereby reducing unwanted systemic effects (e.g. low blood pressure). Use of such soft drug analogs permits the administration of greater doses of the claimed dihydropyridine compounds without subjecting the subject to intolerable levels of unwanted systemic effects.

Specifically, this invention provides compounds of Formula II,

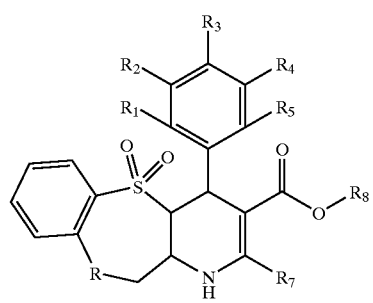

II or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl, and oxadiazole (formed by $R_1$ and $R_2$);

(b) $R_7$ is selected from the group consisting of H, amino, alkyl, aryl, trifluoromethyl, alkoxymethyl, 2-thieno and 3-thieno;

(c) $R_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O)R''', -alkyl-C(O)OR''', -alkyl-N(R'''')C(O)R''' and -alkyl-N(R'''')C(O)OR''', wherein R''' and R'''' are independently selected from the group consisting of hydrogen, amino, alkyl, aryl, aryl-fused cycloalkyl and heterocyclyl, the amino, alkyl, aryl, aryl-fused cycloalkyl and heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, heterocyclyl and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl); and (d) R is SO or $SO_2$.

Each of the embodiments of the compound of Formula I set forth above is also contemplated as an embodiment of the compound of Formula II. In addition, in one embodiment of Formula II, $R_1$, $R_2$, $R_3$, $R_4$, and $R_5$ are independently hydrogen, halogen, trifluoromethyl and $NO_2$. In another embodiment, $R_7$ is methyl. In a further embodiment $R_8$ is -alkyl-OH, alkylamine, lactone, cyclic carbonate, alkyl- or aryl-substituted cyclic carbonate, -aryl-C(O)OR''', -alkyl-aryl-C(O)OR''', -alkyl-C(O)R''', -alkyl-N(R'''')C(O)R''' and -alkyl-N(R'''')C(O)OR'''.

The following compounds are also preferred embodiments of the present invention:

1H-[1,5]benzodithiepino[3,2-b]pyridine-3-carboxylic acid, 4-(2-chloro-6-fluorophenyl)-4,11-dihydro-2-methyl-, 2-(acetyloxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(benzoyloxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[(cyclohexylcarbonyl)oxy]ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[[(1,1-dimethylethoxy)carbonyl]amino]ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-aminoethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, tetrahydro-2-oxo-3-furanyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(2,2-dimethyl-1-oxopropoxy)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-(benzoylamino)ethyl ester, 5,5,10,10-tetraoxide;

1H-[1,5]benzodithiepino[3,2-b]pyridine-3-carboxylic acid, 4-(2-chloro-6-fluorophenyl)-4,11-dihydro-2-methyl-, 2-[[(2S)-2-(6-methoxy-2-naphthalenyl)-1-oxopropyl]oxy]ethyl ester, 5,5,10,10-tetraoxide; and 1H-[1,5]benzodithiepino[3,2-b]pyridine-3-carboxylic acid, 4-(2-chloro-6-fluorophenyl)-4,11-dihydro-2-methyl-, 2-[[(2E)-1-oxo-3-phenyl-2-propenyl]oxy]ethyl ester, 5,5,10,10-tetraoxide.

Unless specified otherwise, the term "alkyl" refers to a straight, branched or cyclic substituent consisting solely of carbon and H with no unsaturation. The term "alkoxy" refers to O-alkyl where alkyl is as defined. Aryl substituents include, for example, phenyl, naphthyl, diphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl, $-(CH_2)_2N(CH_3)CH_2PH$, $-CH_2CH_2-N(Me)-CH_2$, heteroaryl and the like. The term "halo" means fluoro, chloro, bromo and iodo. The symbol "PH" or "Ph" refers to phenyl. "Independently" means that when there are more than one substituent, the substitutents may be different. "Dehydrating agents" used in a solvent such as $CH_2Cl_2$ or toluene include, but are not limited to, sulfuric acid and acetic anhydride.

The compounds of the instant invention are asymmetric in the dihydropyridine ring at the 4-position and thus exist as optical antipodes. As such, all possible optical isomers, antipodes, enantiomers, and diastereomers resulting from additional asymmetric centers that may exist in optical antipodes, racemates and racemic mixtures thereof are also part of this invention. The antipodes can be separated by methods known to those skilled in the art such as, for example, fractional recrystallization of diastereomeric salts of enantiomerically pure acids or diastereomeric salts of enantiomerically pure bases. Alternatively, the antipodes can be separated by chromatography in a Pirkle type column.

As used herein, the phrase "pharmaceutically acceptable salt" means a salt of the free base which possesses the desired pharmacological activity of the free base and which is neither biologically nor otherwise undesirable. These salts may be derived from inorganic or organic acids. Examples of inorganic acids are hydrochloric acid, nitric acid, hydrobromic acid, sulfuric acid, and phosphoric acid. Examples of organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicyclic acid and the like.

The instant compounds can be prepared using readily available starting materials and reaction steps well known in the art (Edema et al. J. Org. Chem. 58: 5624–7, 1993; Howard et al., J. Amer. Chem. Soc. 82:158–64, 1960).

This invention also provides a pharmaceutical composition comprising the instant compound and a pharmaceutically acceptable carrier.

Pharmaceutical compositions containing a compound of the present invention as the active ingredient in intimate admixture with a pharmaceutical carrier can be prepared according to conventional pharmaceutical techniques. The carrier may take a wide variety of forms depending on the form of preparation desired for administration, such as systemic administration including but not limited to intravenous, oral, nasal or parenteral. In preparing the compositions in oral dosage form, any of the usual pharmaceutical carriers may be employed, such as water, glycols, oils, alcohols, flavoring agents, preservatives, coloring agents, syrup and the like in the case of oral liquid preparations (for example, suspensions, elixirs and solutions), and carriers such as starches, sugars, diluents, granulating agents, lubricants, binders, disintegrating agents and the like in the case of oral solid preparations (for example, powders, capsules and tablets).

In one embodiment, the compounds of the instant invention are administered by inhalation. For inhalation administration, the compounds can be in a solution intended for administration by metered dose inhalers, or in a form intended for a dry powder inhaler or insufflator. More particularly, the instant compounds can be conveniently delivered in the form of an aerosol spray from a pressurized container, a pack or a nebuliser with the use of a suitable propellant, e.g., dichlorodifluoromethane, trichlorofluoromethane, dichlorotetrafluoroethane, carbon dioxide or other suitable gas. The dosage unit may be determined by providing a valve to deliver a metered amount. Capsules and cartridges made of a pharmaceutically acceptable material such as gelatin for use in an inhaler or insufflator can be formulated to contain a powder mix of the compound and a suitable powder base such as lactose or starch.

Because of their ease of administration, tablets and capsules represent an advantageous oral dosage unit form wherein solid pharmaceutical carriers are employed. If desired, tablets can be sugar-coated or enteric-coated by standard techniques. For parenterals, the carrier will usually comprise sterile water, though other ingredients to aid solubility or to act as preservatives can be included. Injectable suspensions can also be prepared, wherein appropriate liquid carriers, suspending agents and the like are employed. The instant compounds can also be administered in the form of an aerosol, as discussed above.

In one embodiment, the instant pharmaceutical composition contains a per dosage unit (e.g., tablet, capsule, powder, injection, teaspoonful and the like) from about 0.001 to about 100 mg/kg, and preferably from about 0.01 to about 20 mg/kg of the instant compound. Such dosages can be used both therapeutically and prophylactically.

The compounds of the present invention inhibit the uptake of calcium ions into smooth muscle cells, and therefore act to relax or prevent calcium ion-mediated contraction of smooth muscle tissue.

Thus, this invention further provides a method of treating a subject suffering from a disorder whose alleviation is mediated by the reduction of calcium ion influx into cells whose actions contribute to the disorder, which method comprises administering to the subject a therapeutically effective dose of the instant pharmaceutical composition. By way of example, in a subject suffering from asthma, the subject's airways are constricted due to inflammation of airway smooth muscle cells ("SMC's"). Reducing the calcium influx into the SMC's, whose action (i.e., inflammation) contributes to the disorder, would be expected to alleviate the disorder.

This invention still further provides a method of inhibiting in a subject the onset of a disorder whose alleviation is mediated by the reduction of calcium ion influx into cells whose actions contribute to the disorder, which method comprises administering to the subject a prophylactically effective dose of the instant pharmaceutical composition.

In one embodiment, the disorder is selected from the group consisting of hypersensitivity, allergy, asthma, bronchospasm, dysmenorrhea, esophageal spasm, glaucoma, premature labor, a urinary tract disorder, a gastrointestinal motility disorder and a cardiovascular disorder. The cardiovascular disorder can be, for example, hypertension, ischemia, angina, congestive heart failure, myocardial infarction or stroke. In the preferred embodiment, the disorder is asthma.

As used herein, "treating" a disorder means eliminating or otherwise ameliorating the cause and/or effects thereof. "Inhibiting" the onset of a disorder means preventing, delaying or reducing the likelihood of such onset.

The term "subject" includes, without limitation, any animal or artificially modified animal. In the preferred embodiment, the subject is a human.

Methods are known in the art for determining therapeutically and prophylactically effective doses for the instant pharmaceutical composition. The effective dose for administering the pharmaceutical composition to a human, for example, can be determined mathematically from the results of animal studies.

This invention further provides an apparatus for administering to a subject the instant pharmaceutical composition, comprising a container and the pharmaceutical composition therein, whereby the container has a means for delivering to the subject a therapeutic and/or prophylactic dose of the pharmaceutical composition. In the preferred embodiment, the apparatus is an aerosol spray device for treating and/or preventing asthma via topical respiratory administration.

Finally, this invention provides processes for preparing the compound of Formula I,

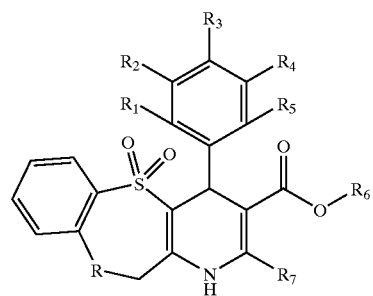

Formula I wherein R is SO. The process comprises the steps of (a) reacting Compound 1a with Compound 1b to form Compound 1c;

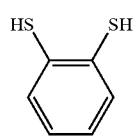

1a

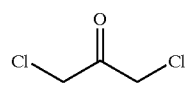

1b

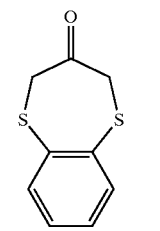

1c

-continued

1d
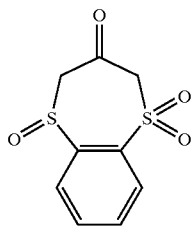

(b) converting Compound 1c to Compound 1d in presence of H$_2$O$_2$ and AcOH; and (c) reacting Compound 1d with Compounds 1f and 1 g to form Compound 1h.

1g
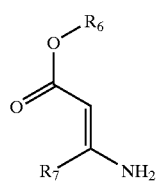

1f
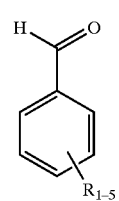

1h
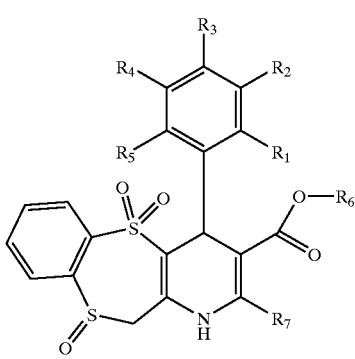

When R is SO$_2$, this process comprises the steps of (a) reacting Compound 1a with Compound 1b to form Compound 1c;

1a
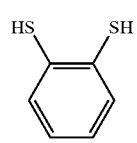

1b
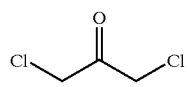

-continued

1c
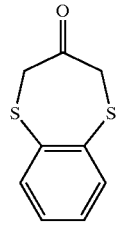

1e
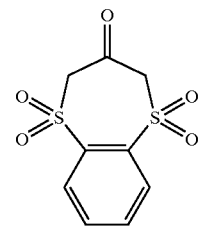

(b) converting Compound 1c to Compound 1e in presence of H$_2$O$_2$, CH$_3$ReO$_3$ and ACOH; and (c) reacting Compound 1e with Compounds 1f and 1 g to form Compound 1i.

1g
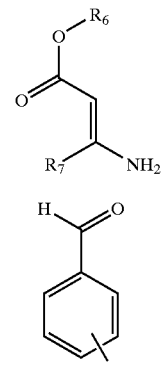

1f

1i
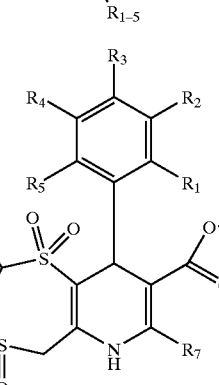

This invention will be better understood by reference to the Experimental Details that follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Experimental Details

A. Schemes and Syntheses

Scheme I shows the preparation of the compounds of Formula I.

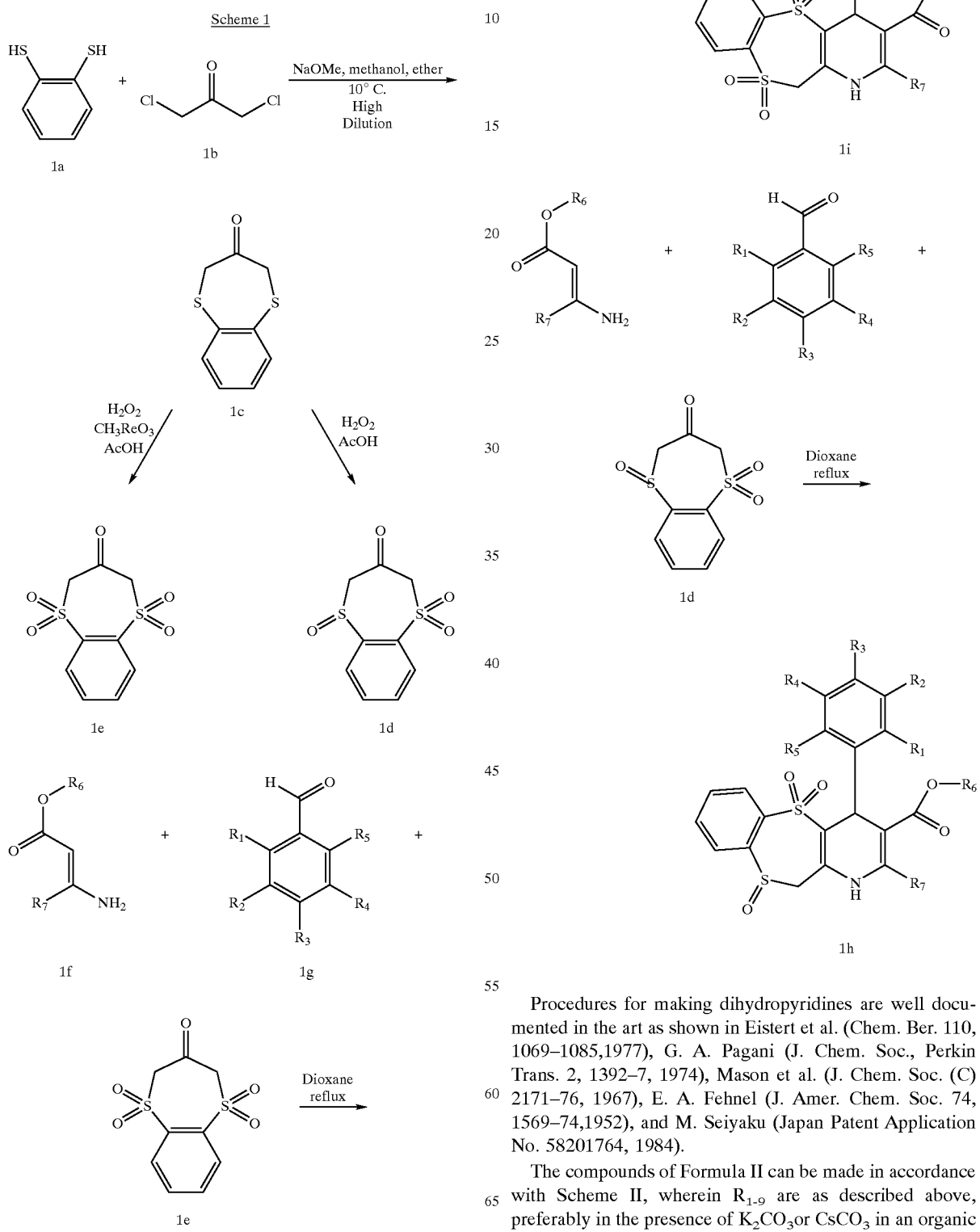

Procedures for making dihydropyridines are well documented in the art as shown in Eistert et al. (Chem. Ber. 110, 1069–1085,1977), G. A. Pagani (J. Chem. Soc., Perkin Trans. 2, 1392–7, 1974), Mason et al. (J. Chem. Soc. (C) 2171–76, 1967), E. A. Fehnel (J. Amer. Chem. Soc. 74, 1569–74,1952), and M. Seiyaku (Japan Patent Application No. 58201764, 1984).

The compounds of Formula II can be made in accordance with Scheme II, wherein $R_{1-9}$ are as described above, preferably in the presence of $K_2CO_3$ or $CsCO_3$ in an organic solvent such as dimethylformamide (DMF).

Scheme II

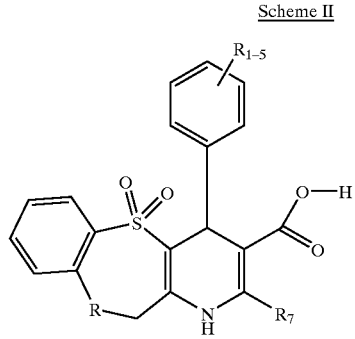

1h or 1i wherein $R_6$ = H

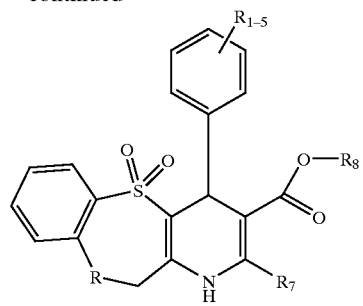

-continued

The compounds of Formula II may also be made in accordance with Scheme III, wherein $R_{1-9}$ are as described above, preferably in the presence of formic acid or NaOH (aq), respectively.

Scheme III

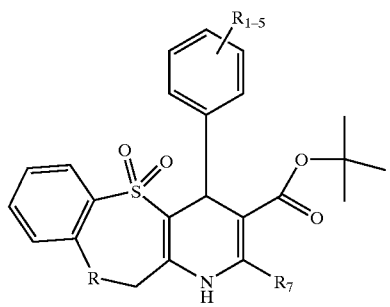

1h or 1i wherein $R_6$ = C(CH)$_3$

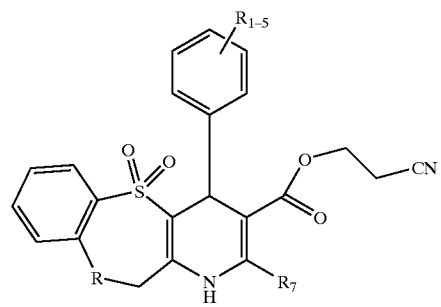

1h or 1i wherein $R_6$ = (CH$_2$)$_2$CN preferably Fromic acid / preferably NaOH(aq)

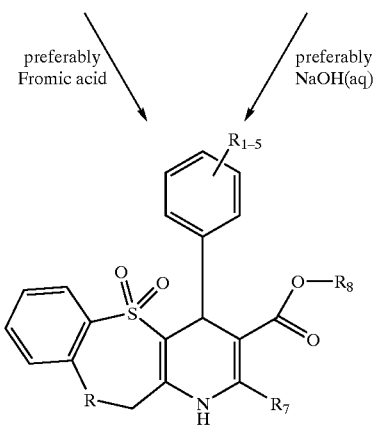

II

The Examples below describe in greater detail the chemical syntheses of representative compounds of the present invention. The rest of the compounds disclosed herein can be prepared similarly in accordance with one or more of these methods. No attempt has been made to optimize the yields obtained in these syntheses, and it would be clear to one skilled in the art that variations in reaction times, temperatures, solvents, and/or reagents could be used to increase such yields.

Table 1 below sets forth the mass spectra data, the inhibition of nitrendipine binding and inhibition of calcium-dependent smooth muscle contraction for selected compounds of Formula I.

TABLE 1

Mass Spectra Data and
Calcium Channel Antagonist Activity for Compounds 1–19

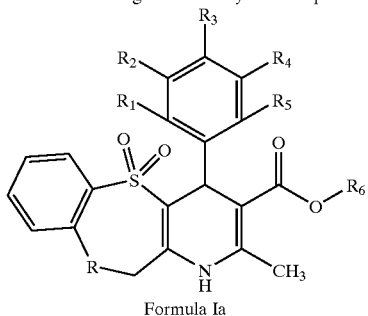

Formula Ia

| Compound No. | $R_1$ | $R_2$ | $R_3$ | $R_4$ | $R_5$ | $R_6$ | R | Mass Spectroscopy | Nitrendipine Binding Assay $IC_{50}$ nM |
|---|---|---|---|---|---|---|---|---|---|
| 1 | H | H | H | H | Cl | Me | SO | M + H = 464 | 14 |
| 2 | H | H | H | Cl | Cl | $(CH_2)_2N(CH_3)CH_2Ph$ | $SO_2$ | M + H = 647 | 20 |
| 3 | $NO_2$ | H | H | H | H | $(CH_2)_2N(CH_3)CH_2Ph$ | $SO_2$ | M + H = 624 | 34 |
| 4 | H | H | H | Cl | H | $(CH_2)_2N(CH_3)CH_2Ph$ | $SO_2$ | M + H = 613 | 22 |
| 5 | H | H | H | H | Cl | Me | $SO_2$ | M + Na = 502 | 9 |
| 6 | H | H | H | Cl | H | Me | SO | M + Na = 486 | 20 |
| 7 | H | H | H | Cl | Cl | Me | SO | M + Na = 520 | 8 |
| 8 | H | H | H | Cl | Cl | Me | $SO_2$ | M + Na = 536 | 22 |
| 9 | H | H | H | Cl | H | Me | $SO_2$ | M + Na = 502 | 10 |
| 10 | H | H | H | H | $NO_2$ | Me | $SO_2$ | M + Na = 513 | 36 |
| 11 | F | F | F | F | F | Me | $SO_2$ | M + Na = 558 | 12 |
| 12 | F | F | F | F | F | $(CH_2)_2N(CH_3)CH_2Ph$ | $SO_2$ | M + H = 669 | 21 |
| 13 | H | H | H | $CF_3$ | F | Me | $SO_2$ | M + Na = 554 | 14 |
| 14 | H | H | H | $CF_3$ | F | $(CH_2)_2N(CH_3)CH_2Ph$ | $SO_2$ | M + H = 665 | 58 |
| 15 | H | H | H | $NO_2$ | H | Me | $SO_2$ | M + Na = 513 | 20 |
| 16 | H | H | H | $NO_2$ | H | $(CH_2)_2N(CH_3)CH_2Ph$ | $SO_2$ | M + H = 624 | 24 |
| 17 | F | H | H | H | Cl | $(CH_2)_2N(CH_3)CH_2Ph$ | $SO_2$ | M + H = 631 | 62 |
| 18 | H | H | H | H | Cl | $(CH_2)_2N(CH_3)CH_2Ph$ | SO | M + H = 597 | 23 |
| 19 | H | H | H | H | Cl | $(CH_2)_2N(CH_3)CH_2Ph$ | $SO_2$ | M + H = 613 | 18 |

EXAMPLE 1

1H-[1,5]Benzodithiepino[3,2-b]pyridine-3-carboxylic acid, 4-(2-chlorophenyl)-4,11-dihydro-2-methyl, 2-[methyl(phenylmethyl)amino]ethyl ester, 5,5,10,10-tetraoxide Scheme IV

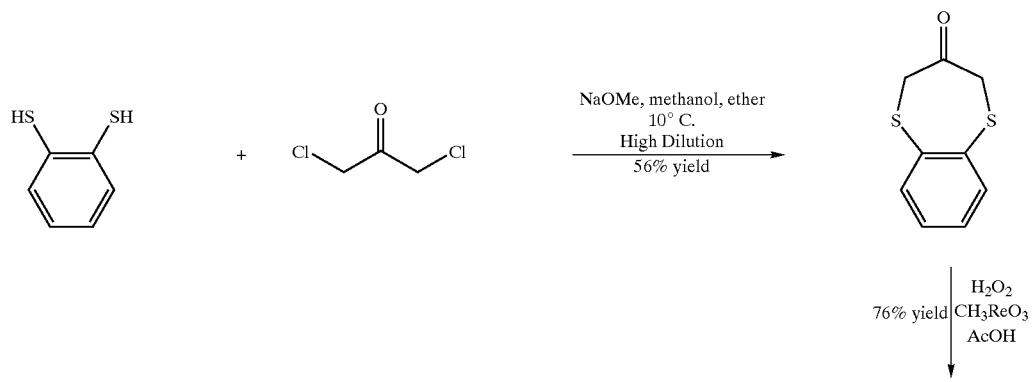

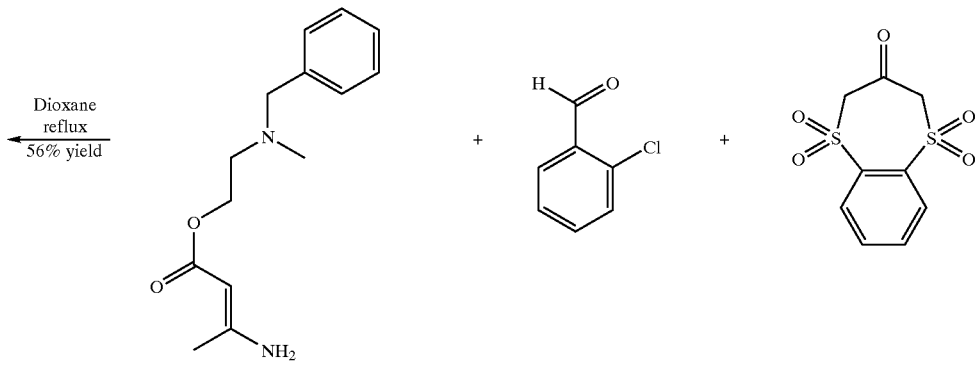

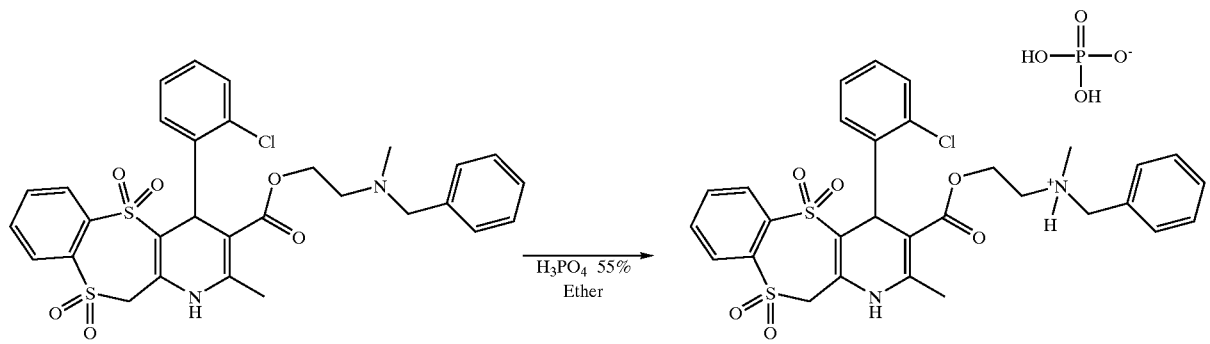

Compound 19

Compound 19 was prepared following Scheme IV above. The details of the preparation are as follows. A solution of 10.55 g (74.17 mmoles) of 1,2-dithiobenzene and 8.01 g (148.34 mmoles) solid sodium methoxide was dissovled in 250 ml methanol. A solution of 9.42 g (74.17 mmoles) of 1,3-dichloroacetone in 250 ml diethyl ether was prepared. Both solutions were added dropwise by addition funnels to 500 ml of a 1:1 mixture of methanol and diethyl ether at 0° C. One hour after all of the reagents were added, 100 ml of 0.5M HCl solution was added. The reaction was then concentrated in vacuo, diluted with 400 ml water and extracted 2×250 ml EtOAc. The organic layers were separated, combined, dried over MgSO$_4$, filtered, and concentrated in vacuo to give a thick red oil. The oil was distilled under vacuum. The distillate was triturated with hexane and the resultant white solid collected by filtration to give 8.20 g of the disulfide.

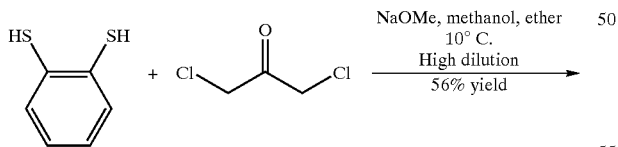

6.04 g (30.77 mmoles) of the disulfide was dissolved in 60 ml of glacial acetic acid containing 0.17 g (1.54 mmoles) of Methyltrioxorhenium (VII). 60 ml of 30% H$_2$O$_2$ solution was then added. The mixture was stirred 72 hours during which time a solid had formed from the solution. The precipitate was collected by filtration, washed with water, diethyl ether and hexane, and dried under vacuum for six hours at 100° C. to give 6.12 g of the benzobissulfone as a white solid.

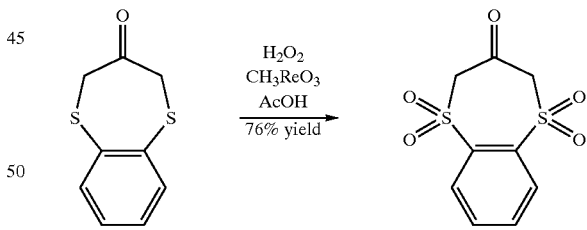

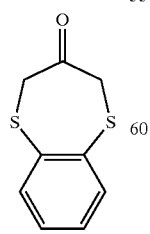

A solution of 3.60 g (13.83 mmoles) of the benzobissulfone, 1.94 g (13.83 mmoles) of 2-chlorobenzaldehyde, and 3.43 g (13.83 mmoles) of 2-(N-Benzyl-N-methylamino)ethyl-3-aminocrotonate in 50 ml dioxane was refluxed for eight hours. The reaction was cooled and the solvent removed in vacuo. The residue was dissolved in 5 ml ethyl acetate and subjected to column chromatography using 2:1 hexane/ethyl acetate as eluent. 4.75 g (7.75 mmoles) of the dihydropyridine was isolated as a yellow-brown foam.

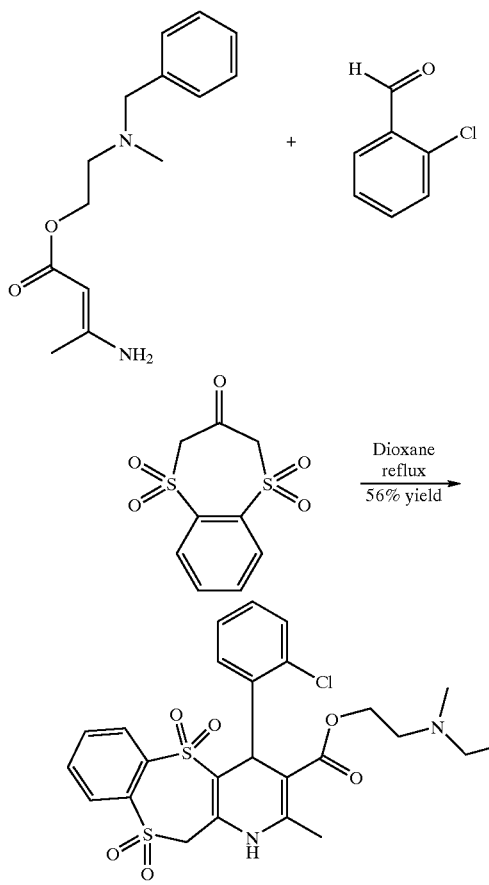

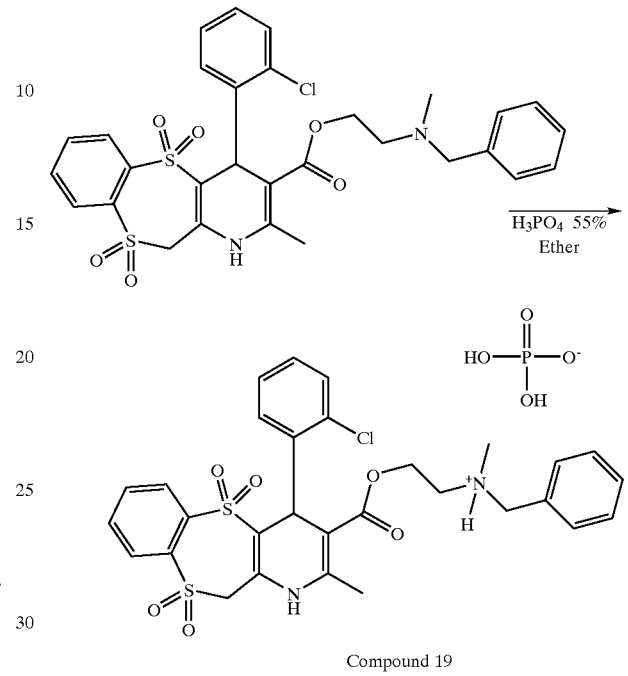

Compound 19

4.75 g (7.75 mmoles) of the dihydropyridine free base was dissolved in 100 ml of diethyl ether. A solution of 0.89 g (7.75 mmoles) of 85% o-orthophosphoric acid in 100 ml diethyl ether was added dropwize by addition funnel. The resultant slurry was stirred three hours and the solid collected by filtration, washed with diethyl ether and hexane to give 2.94 g of the phosphate salt as a light yellow solid.

Table 2 below sets forth the data for mass spectra and the inhibition of nitrendipine binding for selected compounds of Formula II.

TABLE 2

Mass Spectra Data and Calcium Channel Antagonist Activity for Compounds 20–40

Formula IIa

| Compound Number | R | $R_8$ | Nitrendipine Binding $IC_{50}$ (nM) | Mass Spectroscopy M + H/ M + Na |
|---|---|---|---|---|
| 20 | SO | $(CH_2)_2OH$ | 306 | 534 |
| 21 | $SO_2$ | $(CH_2)_2OH$ | 6067 | 550 |
| 22 | $SO_2$ | $(CH_2)_2OC(O)CH_3$ | 180 | 592 |
| 23 | $SO_2$ | $(CH_2)_2OC(O)PH$ | 30 | 654 |
| 24 | $SO_2$ | 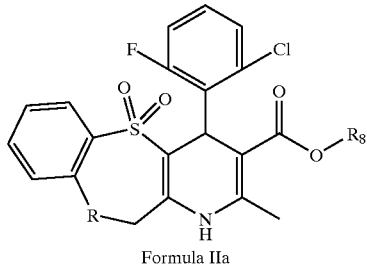 | 43 | 660 |

TABLE 2-continued

Mass Spectra Data and
Calcium Channel Antagonist Activity for Compounds 20–40

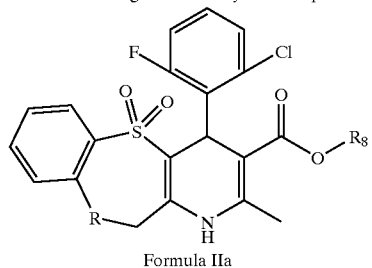

Formula IIa

| Compound Number | R | $R_8$ | Nitrendipine Binding $IC_{50}$ (nM) | Mass Spectroscopy M + H/ M + Na |
|---|---|---|---|---|
| 25 | $SO_2$ | $(CH_2)_2NHC(O)OC(CH_3)_3$ | 420 | 649 |
| 26 | $SO_2$ | $(CH_2)_2NH_2$ | 2000 | 527 |
| 27 | $SO_2$ | $(CH_2)_2OC(O)CH(CH_3)_2$ | 26 | 620 |
| 28 | $SO_2$ | $(CH_2)_2OC(O)C(CH_3)_3$ | 370 | 634 |
| 29 | $SO_2$ | $(CH_2)_2NHC(O)PH$ | 859 | 653 |
| 30 | $SO_2$ | $(CH_2)_2OC(O)CH_2PH$ | 110 | 668 |
| 31 | $SO_2$ | (naproxen propyl ester group) | 209 | 762 |
| 32 | $SO_2$ | (ibuprofen ethyl ester group) | 618 | 738 |
| 33 | $SO_2$ | $(CH_2)_3OH$ | 1435 | 564 |
| 34 | $SO_2$ | $(CH_2)_3OC(O)PH$ | 188 | 668 |
| 35 | $SO_2$ | $(CH_2)_2OC(O)(CH_2)_6PH$ | 60 | 738 |
| 36 | $SO_2$ | $(CH_2)_2OC(O)(CH_2)_9PH$ | 116500 | 780 |
| 37 | $SO_2$ | $(CH_2)_2OC(O)CH=CHPH$ | 101 | 680 |
| 38 | $SO_2$ | (methyl-γ-butyrolactone group) | — | 590 |
| 39 | $SO_2$ | (propyl-γ-butyrolactone group) | — | 618 |
| 40 | $SO_2$ | (ethyl-phenyl-dioxol-one group) | 11 | 680 |

B. Assays

EXAMPLE 2

Assay for Inhibition of Nitrendipine Binding

Female, New Zealand white rabbits (1–2 kg) are sacrificed by cervical dislocation, and the heart is immediately removed, cleaned and chopped into small pieces. The tissue is homogenized in 5×times volume of 0.05M Hepes buffer, pH 7.4. The homogenate is centrifuged at 4000 g for 10 minutes, and the supernatant is re-centrifuged at 42,000×g for 90 minutes. The resulting membrane pellet is resuspended (0.7 ml/g weight) in 0.05M Hepes, pH 7.4 and stored at 70° C. until used. Each tube of the binding assay contains $^3$H-nitrendipine (0.05–0.50 nM), buffer, membranes (0.10 ml), and test compound in a total volume of 1.0 ml. After 90 minutes at 4° C., the bound nitrendipine is separated from the unbound by filtration on Whatman GF/C filters. After rinsing, the filters are dried and counted in a liquid scintillation counter.

Non-specific binding of $^3$H-nitrendipine (that amount bound in the presence of excess unlabelled nitrendipine) is subtracted from the total bound to obtain specifically bound radiolabeled nitrendipine. The amount of specifically bound nitrendipine in the presence of a test compound is compared to that amount bound in the absence of a compound. A percent displacement (or inhibition) can then be calculated.

EXAMPLE 3

Test for Inhibition of Calcium-Dependent Smooth Muscle Contraction

The trachea and the aorta from dogs sacrificed by excess KCl injection are stored overnight at 4° C. in oxygenated Krebs-Henseleit buffer. Tracheal rings, one cartilage segment wide (5–10 mm), are cut starting from the bronchial end. Rings of aorta tissue of the same width are also prepared. After cutting the cartilage, the trachealis muscle tissue and the aorta tissue are suspended in oxygenated Krebs-Henseleit buffer at 37° C. in a 25 ml tissue bath. After a 60-minute equilibration period, the tissues are challenged with 10 $\mu$M carbachol. After 5 minutes, the tissues are rinsed and allowed to rest 50 minutes. The tissues are then challenged with 50 mM KCl and, after 30 minutes, the contractions are quantitated. The tissues are then rinsed and re-equilibrated for 50 minutes. Test compounds are then added for 10 minutes, and the tissue is rechallenged with 50 mM KCl. After 30 minutes, the contraction is recorded. A percent inhibition of smooth muscle contraction can then be calculated.

What is claimed is:

1. A compound of Formula I,

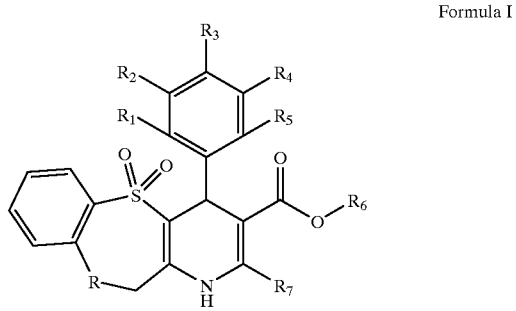

Formula I or a pharmaceutically acceptable salt thereof, wherein
(a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_1$ and $R_2$);
(b) $R_6$ is selected from the group consisting of H, $C_{1-5}$ straight or branched alkyl, aryl, 3-piperidyl, N-substituted 3-piperidyl, N-substituted 2-pyrrolidinyl methylene and substituted alkyl, wherein said N-substituted 3-piperidyl and said N-substituted 2-pyrrolidinyl methylene may be substituted with $C_{1-8}$ straight or branched chain alkyl or benzyl, and said substituted alkyl may be substituted with $C_{1-8}$ alkoxy, $C_{2-8}$ alkanoyloxy, phenylacetyloxy, benzoyloxy, hydroxy, halogen, p-tosyloxy, mesyloxy, amino, carboalkoxy or NR'R", wherein
  (i) R' and R" are independently selected from the group consisting of H, $C_{1-8}$ straight or branched alkyl, $C_{3-7}$ cycloalkyl, phenyl, benzyl and phenethyl, or (ii) R' and R" together form a heterocyclic ring selected from the group consisting of piperidino, pyrrolidino, morpholino, thiomorpholino, piperazino, 2-thieno, 3-thieno and an N-substituted derivative of said heterocyclic rings, said N-substituted derivative being substituted with H, $C_{1-8}$ straight or branched alkyl, benzyl, benzhydryl, phenyl and/or substituted phenyl (substituted with $NO_2$, halogen, $C_{1-8}$ straight or branched chain alkyl, $C_{1-8}$ alkoxy and/or trifluoromethyl);
(c) $R_7$ is selected from the group consisting of H, amino, alkyl, aryl, trifluoromethyl, alkoxymethyl, 2-thieno and 3-thieno; and
(d) R is SO or $SO_2$.

2. The compound of claim 1, wherein $R_6$ is —$(CH_2)_2$N$(CH_3)CH_2$PH.

3. The compound of claim 1, wherein $R_6$ is methyl.

4. The compound of claim 3, wherein $R_4$ and $R_5$ are Cl, $R_7$ is methyl, and R is SO.

5. The compound of claim 3, wherein $R_5$ is Cl, $R_7$ is methyl, and R is $SO_2$.

6. The compound of claim 1 which is 1H-[1,5] Benzodithiepino[3,2-b]pyridine-3-carboxylic acid, 4-(2-chlorophenyl)-4,11-dihydro-2-methyl, methyl ester, 5,5,10-trioxide.

7. The compound of claim 1 which is 1H-[1,5] Benzodithiepino[3,2-b]pyridine-3-carboxylic acid, 4,11-dihydro-2-methyl-4-(2-nitrophenyl), 2-[methyl (phenylmethyl)amino]ethyl ester, 5,5,10,10-tetraoxide.

8. The compound of claim 1 which is 1H-[1,5] Benzodithiepino[3,2-b]pyridine-3-carboxylic acid, 4-(3-chlorophenyl)-4,11-dihydro-2-methyl, 2-[methyl (phenylmethyl)amino]ethyl ester, 5,5,10,10-tetraoxide.

9. The compound of claim 1 which is 1H-[1,5] Benzodithiepino[3,2-b]pyridine-3-carboxylic acid, 4-(2-chlorophenyl)-4,11-dihydro-2-methyl, methyl ester, 5,5,10, 10-tetraoxide.

10. The compound of claim 1 which is 1H-[1,5] Benzodithiepino[3,2-b]pyridine-3-carboxylic acid, 4-(2-chlorophenyl)-4,11-dihydro-2-methyl, methyl ester, 5,5,10, 10-tetraoxide.

11. The compound of claim 1 which is 1H-[1,5] Benzodithiepino[3,2-b]pyridine-3-carboxylic acid, 4-(3-chlorophenyl)-4,11-dihydro-2-methyl, methyl ester, 5,5,10-trioxide.

12. The compound of claim 1 which is 1H-[1,5] Benzodithiepino[3,2-b]pyridine-3-carboxylic acid, 4-(2,3-dichlorophenyl)-4,11-dihydro-2-methyl, methyl ester, 5,5, 10-trioxide.

13. The compound of claim 1 which is 1H-[1,5] Benzodithiepino[3,2-b]pyridine-3-carboxylic acid, 4-(2,3-dichlorophenyl)-4,11-dihydro-2-methyl, methyl ester, 5,5, 10,10-tetraoxide.

14. The compound of claim 1 which is 1H-[1,5] Benzodithiepino[3,2-b]pyridine-3-carboxylic acid, 4-(3-chlorophenyl)-4,11-dihydro-2-methyl, methyl ester, 5,5,10, 10- tetraoxide.

15. The compound of claim 1 which is 1H-[1,5] Benzodithiepino[3,2-b]pyridine-3-carboxylic acid, 4,11-dihydro-2-methyl-4-(3-nitrophenyl), methyl ester, 5,5,10, 10-tetraoxide.

16. The compound of claim 1 which is 1H-[1,5] Benzodithiepino[3,2-b]pyridine-3-carboxylic acid, 4,11-dihydro-2-methyl4-(pentafluorophenyl), methyl ester, 5,5,10,10-tetraoxide.

17. The compound of claim 1 which is 1H-[1,5] Benzodithiepino[3,2-b]pyridine-3-carboxylic acid, 4,11-dihydro-2-methyl-4-(pentafluorophenyl), 2-[methyl(phenylmethyl)amino]ethyl ester, 5,5,10,10-tetraoxide.

18. The compound of claim 1 which is 1H-[1,5] Benzodithiepino[3,2-b]pyridine-3-carboxylic acid, 4-[2-fluoro-3-(trifluoromethyl)phenyl]-4,11-dihydro-2-methyl, methyl ester, 5,5,10,10-tetraoxide.

19. The compound of claim 1 which is 1H-[1,5] Benzodithiepino[3,2-b]pyridine-3-carboxylic acid, 4-[2-fluoro-3-(trifluoromethyl)phenyl]-4,11-dihydro-2-methyl, 2-[methyl(phenylmethyl)amino]ethyl ester, 5,5,10,10-tetraoxide.

20. The compound of claim 1 which is 1H-[1,5] Benzodithiepino[3,2-b]pyridine-3-carboxylic acid, 4,11-dihydro-2-methyl-4-(3-nitrophenyl), methyl ester, 5,5,10,10-tetraoxide.

21. The compound of claim 1 which is 1H-[1,5] Benzodithiepino[3,2-b]pyridine-3-carboxylic acid, 4,11-dihydro-2-methyl-4-(3-nitrophenyl), 2-[methyl(phenylmethyl)amino]ethyl ester, 5,5,10,10-tetraoxide.

22. The compound of claim 1 which is 1H-[1,5] Benzodithiepino[3,2-b]pyridine-3-carboxylic acid, 4-(2-chloro-6-fluorophenyl)-4,11-dihydro-2-methyl, 2-[methyl(phenylmethyl)amino]ethyl ester, 5,5,10,10-tetraoxide.

23. The compound of claim 1 which is 1H-[1,5] Benzodithiepino[3,2-b]pyridine-3-carboxylic acid, 4-(2-chlorophenyl)-4,11-dihydro-2-methyl, 2-[methyl(phenylmethyl)amino]ethyl ester, 5,5,10-trioxide.

24. The compound of claim 1 which is 1H-[1,5] Benzodithiepino[3,2-b]pyridine-3-carboxylic acid, 4-(2-chlorophenyl)-4,11-dihydro-2-methyl, 2-[methyl(phenylmethyl)amino]ethyl ester, 5,5,10,10-tetraoxide.

25. The compound of claim 1 which is 1H-[1,5] Benzodithiepino[3,2-b]pyridine-3-carboxylic acid, 4-(2,3-dichlorophenyl)-4,11-dihydro-2-methyl, 2-[methyl(phenylmethyl)amino]ethyl ester, 5,5,10,10-tetraoxide.

26. A compound of Formula II,

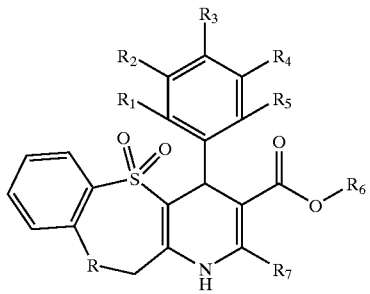

II or a pharmaceutically acceptable salt thereof, wherein (a) $R_1$, $R_2$, $R_3$, $R_4$ and $R_5$ are independently selected from the group consisting of H, OH, halogen, cyano, $NO_2$, alkyl, $C_{1-8}$ alkoxy, $C_{1-8}$ alkylsulfonyl, $C_{1-4}$ carboalkoxy, $C_{1-8}$ alkylthio, difluoromethoxy, difluoromethylthio, trifluoromethyl and oxadiazole (formed by $R_1$ and $R_2$);

(b) $R_7$ is selected from the group consisting of H, amino, alkyl, aryl, trifluoromethyl, alkoxymethyl, 2-thieno and 3-thieno;

(c) $R_8$ is selected from the group consisting of -alkyl-OH, alkylamine, lactone, cyclic carbonate, alkyl-substituted cyclic carbonate, aryl-substituted cyclic carbonate, -aryl-C(O)OR''', -alkyl-aryl-C(O)OR''', -alkyl-OC(O)R''', -alkyl-C(O)R''', -alkyl-C(O)OR''', -alkyl-N(R'''')C(O)R''' and -alkyl-N(R'''')C(O)OR''', wherein R''' and R'''' are independently selected from the group consisting of hydrogen, amino, alkyl, aryl, aryl-fused cycloalkyl and the amino, alkyl, aryl, aryl-fused cycloalkyl heterocyclyl being optionally substituted with halogen, cyano, $NO_2$, lactone, amino, alkylamino, aryl-substituted alkylamino, amide, carbamate, carbamoyl, cyclic carbonate, alkyl, halogen-substituted alkyl, arylalkyl, alkoxy, and/or aryl (the aryl being optionally substituted with OH, halogen, cyano, $NO_2$, alkyl, amino, dimethylamino, alkoxy, alkylsulfonyl, $C_{1-4}$ carboalkoxy, alkylthio and/or trifluoromethyl); and (d) R is SO or $SO_2$.

27. The compound of claim 26, wherein $R_1$, $R_2$, $R_3$, $R_4$ and $R_5$ are independently selected from the group consisting of hydrogen, halogen, trifluoromethyl and $NO_2$.

28. The compound of claim 26, wherein $R_7$ is methyl.

29. The compound of claim 26, wherein $R_8$ is selected from the group consisting of -alkyl-OH, alkylamine, lactone, cyclic carbonate, alkyl- or aryl-substituted cyclic carbonate, -aryl-C(O)OR''', -alkyl-aryl-C(O)OR''', -alkyl-C(O)R''', -alkyl-N(R'''')C(O)R''' and -alkyl-N(R'''')C(O)OR'''.

30. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-(acetyloxy)ethyl ester, 5,5,10,10-tetraoxide.

31. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-(benzoyloxy)ethyl ester, 5,5,10,10-tetraoxide.

32. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-[(cyclohexylcarbonyl)oxy]ethyl ester, 5,5,10,10-tetraoxide.

33. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-[[(1,1-dimethylethoxy)carbonyl]amino]ethyl ester, 5,5,10,10-tetraoxide.

34. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-aminoethyl ester, 5,5,10,10-tetraoxide.

35. The compound of claim 26 which is 1H-[1,5] benzodithiepino[3,2-b]pyridine-3-carboxylic acid, 4-(2-chloro-6-fluorophenyl)-4,11-dihydro-2-methyl-, tetrahydro-2-oxo-3-furanyl ester, 5,5,10,10-tetraoxide.

36. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-(2,2-dimethyl-1-oxopropoxy)ethyl ester, 5,5,10,10-tetraoxide.

37. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-(benzoylamino)ethyl ester, 5,5,10,10-tetraoxide.

38. The compound of claim 26 which is 1H-[1,5] benzodithiepino[3,2-b]pyridine-3-carboxylic acid, 4-(2-chloro-6-fluorophenyl)-4,11-dihydro-2-methyl-, 2-[[(2S)-2-(6-methoxy-2-naphthalenyl)-1-oxopropyl]oxy]ethyl ester, 5,5,10,10-tetraoxide.

39. The compound of claim 26 which is 1H-[1,5]benzodithiepino[3,2-b]pyridine-3-carboxylic acid, 4-(2-chloro-6-fluorophenyl)-4,11-dihydro-2-methyl-, 2-[[(2E)-1-oxo-3-phenyl-2-propenyl]oxy]ethyl ester, 5,5,10,10-tetraoxide.

40. A pharmaceutical composition comprising the compound of claim 1 or 26 and a pharmaceutically acceptable carrier.

41. A process for preparing the compound of claim 1 wherein R is SO, which process comprises:

(a) reacting Compound 1a with Compound 1b to form Compound 1c;

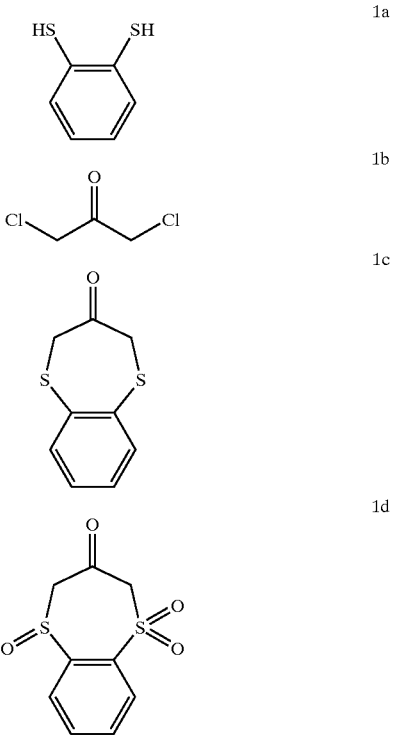

(b) converting Compound 1c to Compound 1d in presence of $H_2O_2$ and AcOH; and
(c) reacting Compound 1d with Compounds 1f and 1g to form the compound of claim 1 wherein R is SO.

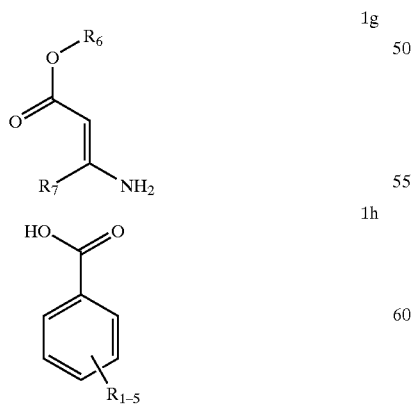

42. A process for preparing the compound of claim 1 wherein R is $SO_2$, which process comprises:

(a) reacting Compound 1a with Compound 1b to form Compound 1c;

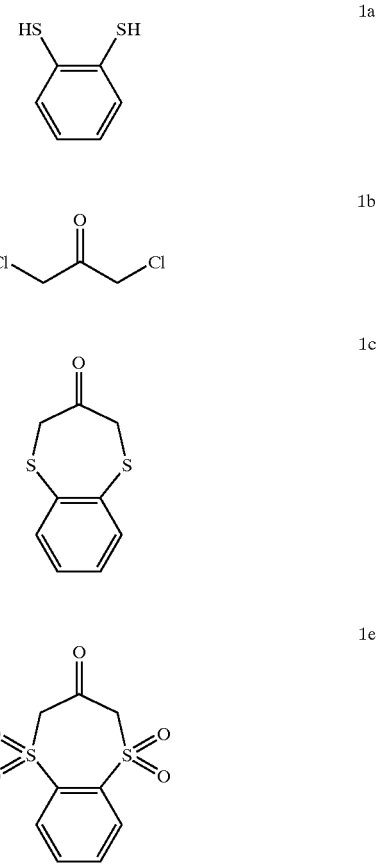

(b) converting Compound 1c to Compound 1e in presence of $H_2O_2$, $CH_3ReO_3$ and AcOH; and
(c) reacting Compound 1e with Compounds 1f and 1g to form the compound of claim 1 wherein R is $SO_2$,

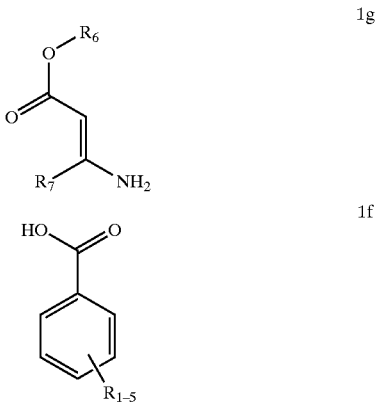

* * * * *